US009205251B2

(12) United States Patent
Govea et al.

(10) Patent No.: US 9,205,251 B2
(45) Date of Patent: Dec. 8, 2015

(54) SYSTEMS AND METHODS FOR INPUTTING FLUID INTO A LEAD OF AN ELECTRICAL STIMULATION SYSTEM

(71) Applicant: BOSTON SCIENTIFIC NEUROMODULATION CORPORATION, Valencia, CA (US)

(72) Inventors: Michael Govea, Glendale, CA (US); Matthew Lee McDonald, Pasadena, CA (US); John Michael Barker, Ventura, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 87 days.

(21) Appl. No.: 14/179,305

(22) Filed: Feb. 12, 2014

(65) Prior Publication Data

US 2014/0277314 A1 Sep. 18, 2014

Related U.S. Application Data

(60) Provisional application No. 61/780,291, filed on Mar. 13, 2013.

(51) Int. Cl.
*A61N 1/00* (2006.01)
*A61N 1/05* (2006.01)
*A61N 1/08* (2006.01)

(52) U.S. Cl.
CPC ............. *A61N 1/05* (2013.01); *A61N 1/0553* (2013.01); *A61N 1/08* (2013.01); *A61N 2001/086* (2013.01)

(58) Field of Classification Search
CPC .......... A61N 1/05; A61N 1/08; A61N 1/0553; A61N 1/0568; A61B 2562/244
See application file for complete search history.

(56) References Cited

U.S. PATENT DOCUMENTS

| | | | |
|---|---|---|---|
| 5,531,679 A * | 7/1996 | Schulman et al. | ............... 604/65 |
| 6,181,969 B1 | 1/2001 | Gord | |
| 6,516,227 B1 | 2/2003 | Meadows et al. | |
| 6,609,029 B1 | 8/2003 | Mann et al. | |
| 6,609,032 B1 | 8/2003 | Woods et al. | |
| 6,632,221 B1 * | 10/2003 | Edwards et al. | ................ 606/41 |
| 6,741,892 B1 | 5/2004 | Meadows et al. | |
| 7,244,150 B1 | 7/2007 | Brase et al. | |
| 7,672,734 B2 | 3/2010 | Anderson et al. | |
| 7,761,165 B1 | 7/2010 | He et al. | |
| 7,949,395 B2 | 5/2011 | Kuzma | |

(Continued)

OTHER PUBLICATIONS

U.S. Appl. No. 13/962,282, filed Aug. 8, 2013.

*Primary Examiner* — Michael Kahelin
*Assistant Examiner* — Mallika D Fairchild
(74) *Attorney, Agent, or Firm* — Lowe Graham Jones PLLC; Bruce E. Black

(57) ABSTRACT

An insertion kit for an electrical stimulation system includes a lead with a lead body and a jacket disposed over at least a portion of the lead body. Apertures are defined along an outer surface of the lead body with each of the apertures extending completely through the jacket to an inner surface. The apertures include at least one first aperture. Conductors electrically couple electrodes and terminals disposed along the lead. Conductor insulation is disposed over each of the conductors. At least a portion of the conductor insulation is in fluid communication with the local environment external to the lead via the apertures. A fluid-insertion assembly is configured and arranged for inputting fluid into the lead, via the at least one first aperture, prior to implantation of the lead into the patient.

19 Claims, 8 Drawing Sheets

(56) References Cited

U.S. PATENT DOCUMENTS

| | | |
|---|---|---|
| 8,224,450 B2 | 7/2012 | Brase |
| 2004/0024371 A1* | 2/2004 | Plicchi et al. .................. 604/264 |
| 2004/0059392 A1 | 3/2004 | Parramon et al. |
| 2005/0165465 A1 | 7/2005 | Pianca et al. |
| 2005/0222657 A1* | 10/2005 | Wahlstrand et al. .......... 607/116 |
| 2007/0150036 A1 | 6/2007 | Anderson |
| 2007/0219595 A1 | 9/2007 | He |
| 2007/0239243 A1 | 10/2007 | Moffitt et al. |
| 2008/0071320 A1 | 3/2008 | Brase |
| 2008/0161795 A1* | 7/2008 | Wang et al. ..................... 606/41 |

\* cited by examiner

SYSTEMS AND METHODS FOR INPUTTING FLUID INTO A LEAD OF AN ELECTRICAL STIMULATION SYSTEM

CROSS-REFERENCE TO RELATED APPLICATIONS

This application claims the benefit under 35 U.S.C. §119 (e) of U.S. Provisional Patent Application Ser. No. 61/780,291 filed Mar. 13, 2013, which is incorporated herein by reference.

FIELD

The present invention is directed to the area of implantable electrical stimulation systems and methods of making and using the systems. The present invention is also directed to implantable electrical stimulation systems having leads and fluid-insertion assemblies for inputting fluid into the leads, as well as methods of making and using the leads, fluid-insertion assemblies, and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in operational contact with or near the nerves, muscles, or other tissue to be stimulated. The pulse generator in the control module generates electrical pulses that are delivered by the electrodes to body tissue.

Conventional implanted electrical stimulation systems are not safe in magnetic resonance imaging (MRI) environment due to the high strength magnetic field and the fluctuations in the magnetic fields caused by radio frequency (RF) pulses used during the MRI procedure. The leads have the permittivity and the conductivity different from that of the interstitial fluid. During the MRI scan, the magnetic fields generated by the RF pulses interact with the lead and induce eddy currents thereby creating unwanted heating of the lead and hence damaging the surrounding tissue. The interaction may also lead to undesired functioning of the electronic components, thereby delivering deleterious stimulations, or premature failure of electronic components.

BRIEF SUMMARY

In one embodiment, an insertion kit for an electrical stimulation system includes a lead configured and arranged for insertion into a patient. The lead includes a lead body having a distal end portion, a proximal end portion, and a longitudinal length. A jacket is disposed over at least a portion of the longitudinal length of the lead body. The jacket has an outer surface and an opposing inner surface. At least a portion of the outer surface of the jacket forms at least a portion of an outer surface of the lead body. At least a portion of the inner surface of the jacket is open to the lead body. Apertures are defined along the outer surface of the lead body with each of the apertures extending completely through the jacket to the inner surface. The apertures include at least one first aperture. Electrodes are disposed along the distal end portion of the lead body. Terminals are disposed along the proximal end portion of the lead body. Conductors electrically couple the electrodes to the terminals. Conductor insulation is disposed over each of the conductors. At least a portion of the conductor insulation is in fluid communication with the local environment external to the lead via the apertures. A fluid-insertion assembly is configured and arranged for inputting fluid into the lead, via the at least one first aperture, prior to implantation of the lead into the patient.

In another embodiment, a method of implanting an electrical stimulation lead includes providing a lead that includes a jacket that is disposed over at least a portion of a longitudinal length of a lead body of the lead and that forms at least a portion of an outer surface of the lead body. The lead defines apertures disposed along the outer surface of the lead body with each of the apertures extending completely through the jacket. The apertures include at least one first aperture. The lead further includes electrodes disposed along a distal end portion of the lead body. Terminals are disposed along a proximal end portion of the lead body. Conductors electrically couple the electrodes to the terminals. Conductor insulation is disposed over each of the conductors. At least a portion of the conductor insulation is in fluid communication with the local environment external to the lead, via the apertures. Fluid is input into the at least one first aperture using a fluid-insertion assembly. The lead, with input fluid, is advanced to a target stimulation location within a patient.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to implantable electrical stimulation systems having leads and fluid-insertion assemblies for inputting fluid into the leads, as well as methods of making and using the leads, fluid-insertion assemblies, and electrical stimulation systems.

Suitable implantable electrical stimulation systems include, but are not limited to, a least one lead with one or more electrodes disposed along a distal end of the lead and one or more terminals disposed along the one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,949,395; 7,244,150; 7,672,734; and 7,761,165; and U.S. Patent Applications Publication Nos. 2005/0165465; 2007/0150036; 2007/0219595; 2007/0239243; and 2008/0071320, all of which are incorporated by reference.

Figure 1:
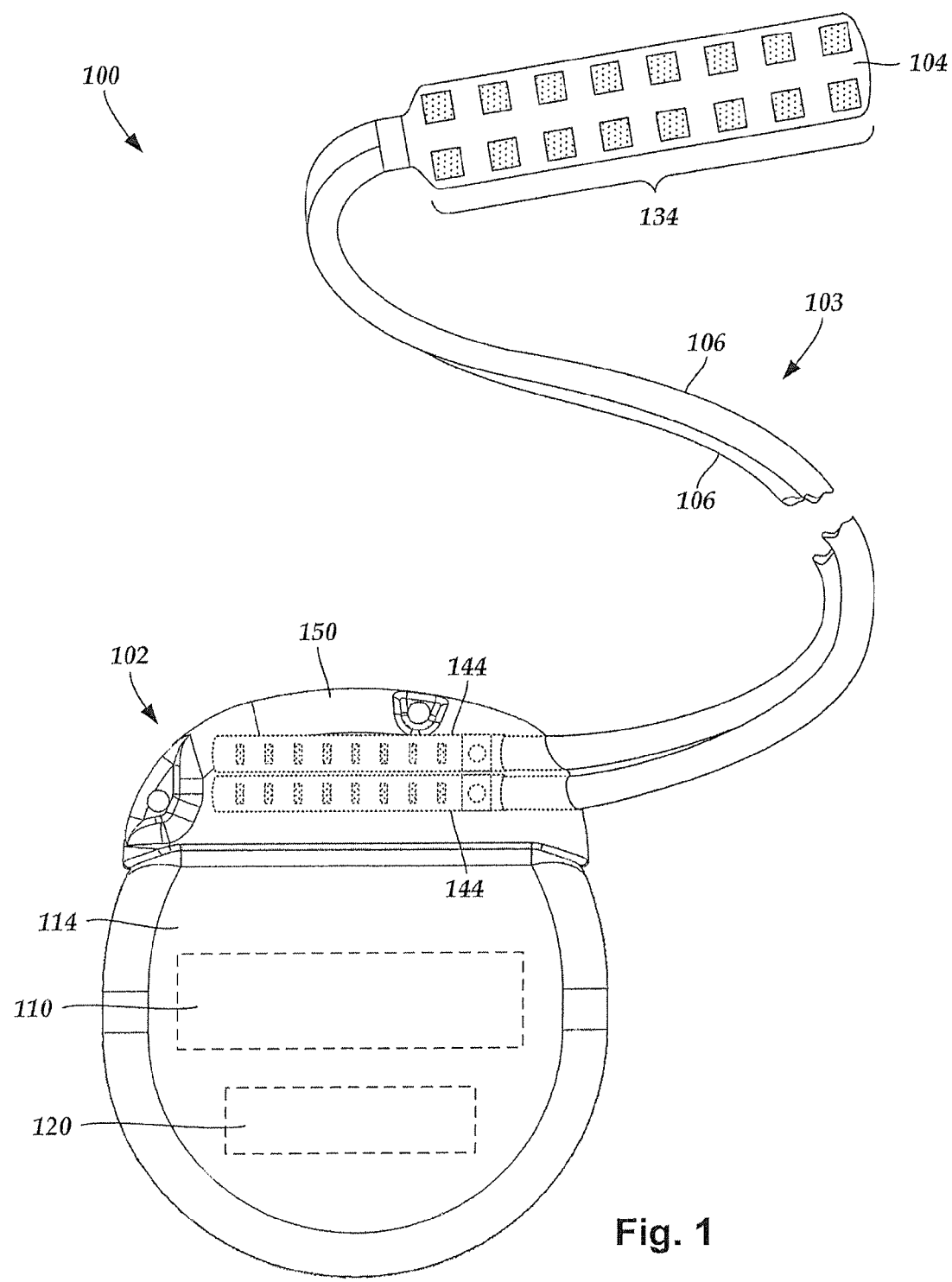
FIG. 1 is a schematic view of one embodiment of an electrical stimulation system that includes a paddle lead electrically coupled to a control module, according to the invention.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes a paddle body 104 and one or more lead bodies 106. In FIG. 1, the lead 103 is shown having two lead bodies 106. It will be understood that the lead 103 can include any suitable number of lead bodies including, for example, one, two, three, four, five, six, seven, eight or more lead bodies 106. An array of electrodes 133, such as electrode 134, is disposed on the paddle body 104, and an array of terminals (e.g., 210 in FIG. 2A-2B) is disposed along each of the one or more lead bodies 106.

It will be understood that the electrical stimulation system can include more, fewer, or different components and can have a variety of different configurations including those configurations disclosed in the electrical stimulation system references cited herein. For example, instead of a paddle body, the electrodes can be disposed in an array at or near the distal end of a lead body forming a percutaneous lead.

Figure 2:
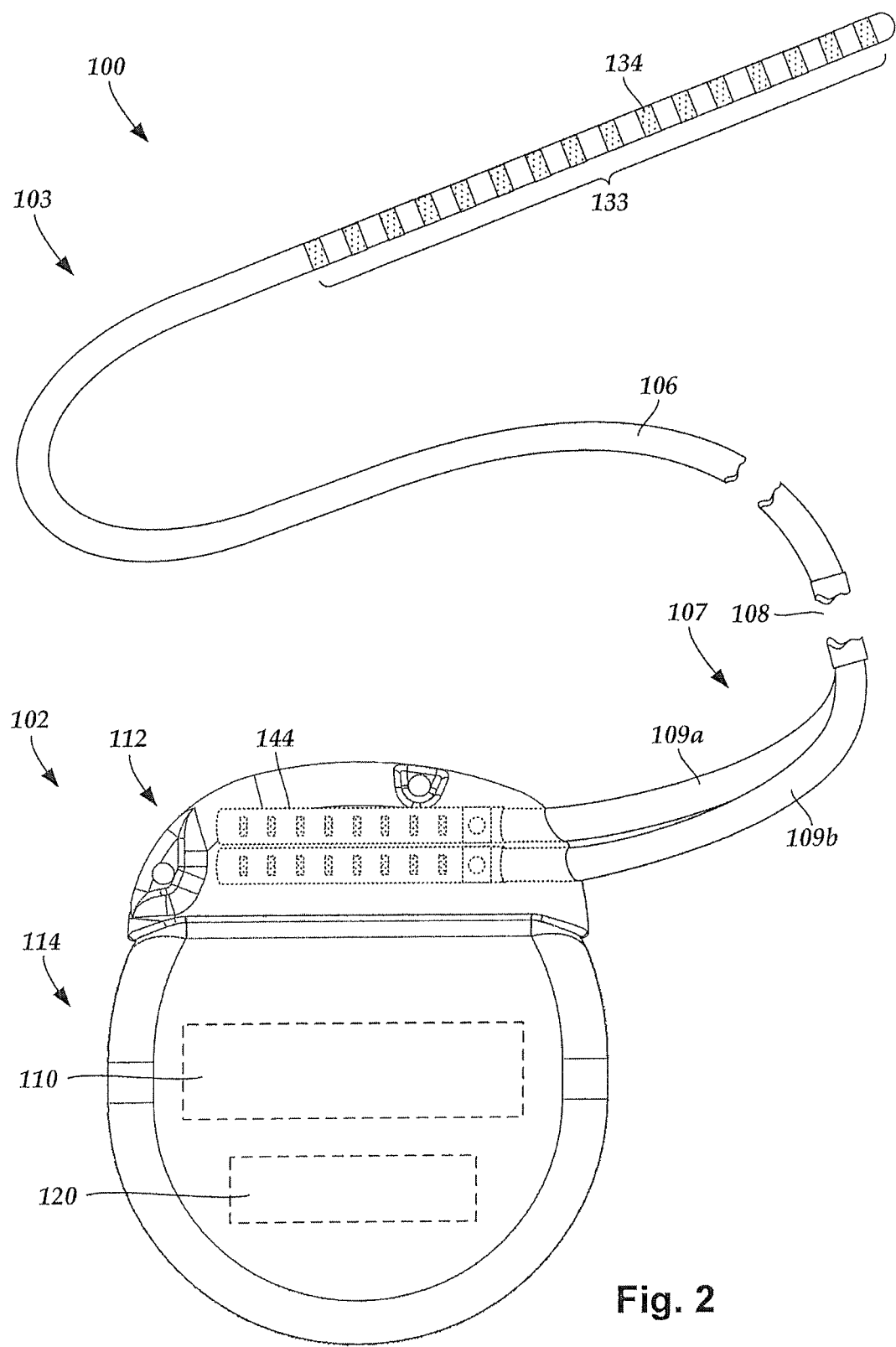
FIG. 2 is a schematic view of one embodiment of an electrical stimulation system that includes a percutaneous lead electrically coupled to a control module, according to the invention.

FIG. 2 illustrates schematically another embodiment of the electrical stimulation system 100, where the lead 103 is a percutaneous lead. In FIG. 2, the electrodes 134 are shown disposed along the one or more lead bodies 106. In at least some embodiments, the lead 103 is isodiametric along a longitudinal length of the lead body 106.

The lead 103 can be coupled to the control module 102 in any suitable manner. In FIG. 1, the lead 103 is shown coupling directly to the control module 102. In at least some other embodiments, the lead 103 couples to the control module 102 via one or more intermediate devices (300 in FIGS. 3A-3B). For example, in at least some embodiments one or more lead extensions 324 (see e.g., FIG. 3B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

In FIG. 2, the electrical stimulation system 100 is shown having a splitter 207 configured and arranged for facilitating coupling of the lead 103 to the control module 102. The splitter 207 includes a splitter connector 208 configured to couple to a proximal end of the lead 103, and one or more splitter tails 209a and 209b configured and arranged to couple to the control module 102 (or another splitter, a lead extension, an adaptor, or the like).

The control module 102 typically includes a connector housing 112 and a sealed electronics housing 114. An electronic subassembly 110 and an optional power source 120 are disposed in the electronics housing 114. A control module connector 144 is disposed in the connector housing 112. The control module connector 144 is configured and arranged to make an electrical connection between the lead 103 and the electronic subassembly 110 of the control module 102.

The electrical stimulation system or components of the electrical stimulation system, including the paddle body 104, the one or more of the lead bodies 106, and the control module 102, are typically implanted into the body of a patient. The electrical stimulation system can be used for a variety of applications including, but not limited to deep brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium.

Any suitable number of electrodes 134 can be disposed on the lead including, for example, four, five, six, seven, eight, nine, ten, eleven, twelve, fourteen, sixteen, twenty-four, thirty-two, or more electrodes 134. In the case of paddle leads, the electrodes 134 can be disposed on the paddle body 104 in any suitable arrangement. In FIG. 1, the electrodes 134 are arranged into two columns, where each column has eight electrodes 134.

The electrodes of the paddle body 104 (or one or more lead bodies 106) are typically disposed in, or separated by, a non-conductive, biocompatible material such as, for example, silicone, polyurethane, polyetheretherketone ("PEEK"), epoxy, and the like or combinations thereof. The one or more lead bodies 106 and, if applicable, the paddle body 104 may be formed in the desired shape by any process including, for example, molding (including injection molding), casting, and the like. The non-conductive material typically extends from the distal ends of the one or more lead bodies 106 to the proximal end of each of the one or more lead bodies 106.

In the case of paddle leads, the non-conductive material typically extends from the paddle body 104 to the proximal end of each of the one or more lead bodies 106. Additionally, the non-conductive, biocompatible material of the paddle body 104 and the one or more lead bodies 106 may be the same or different. Moreover, the paddle body 104 and the one or more lead bodies 106 may be a unitary structure or can be formed as two separate structures that are permanently or detachably coupled together.

Figure 3A:
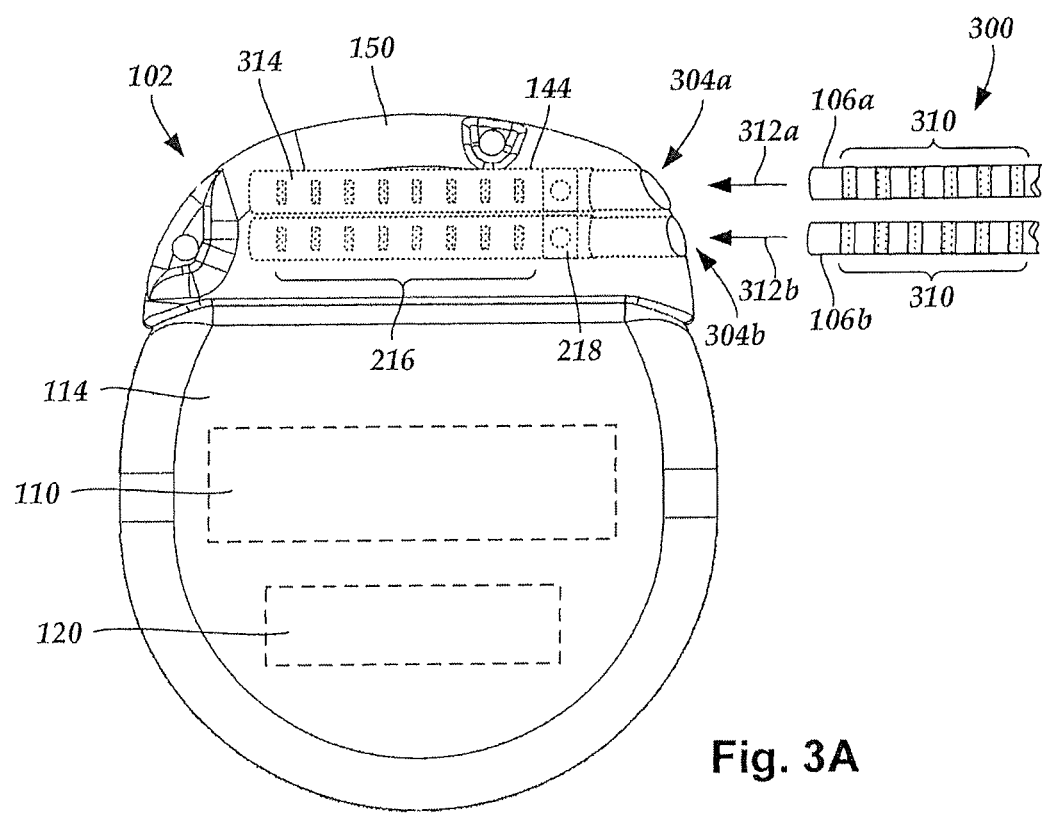
FIG. 3A is a schematic view of one embodiment of the control module of FIG. 1 configured and arranged to electrically couple to an elongated device, according to the invention.
Figure 3B:
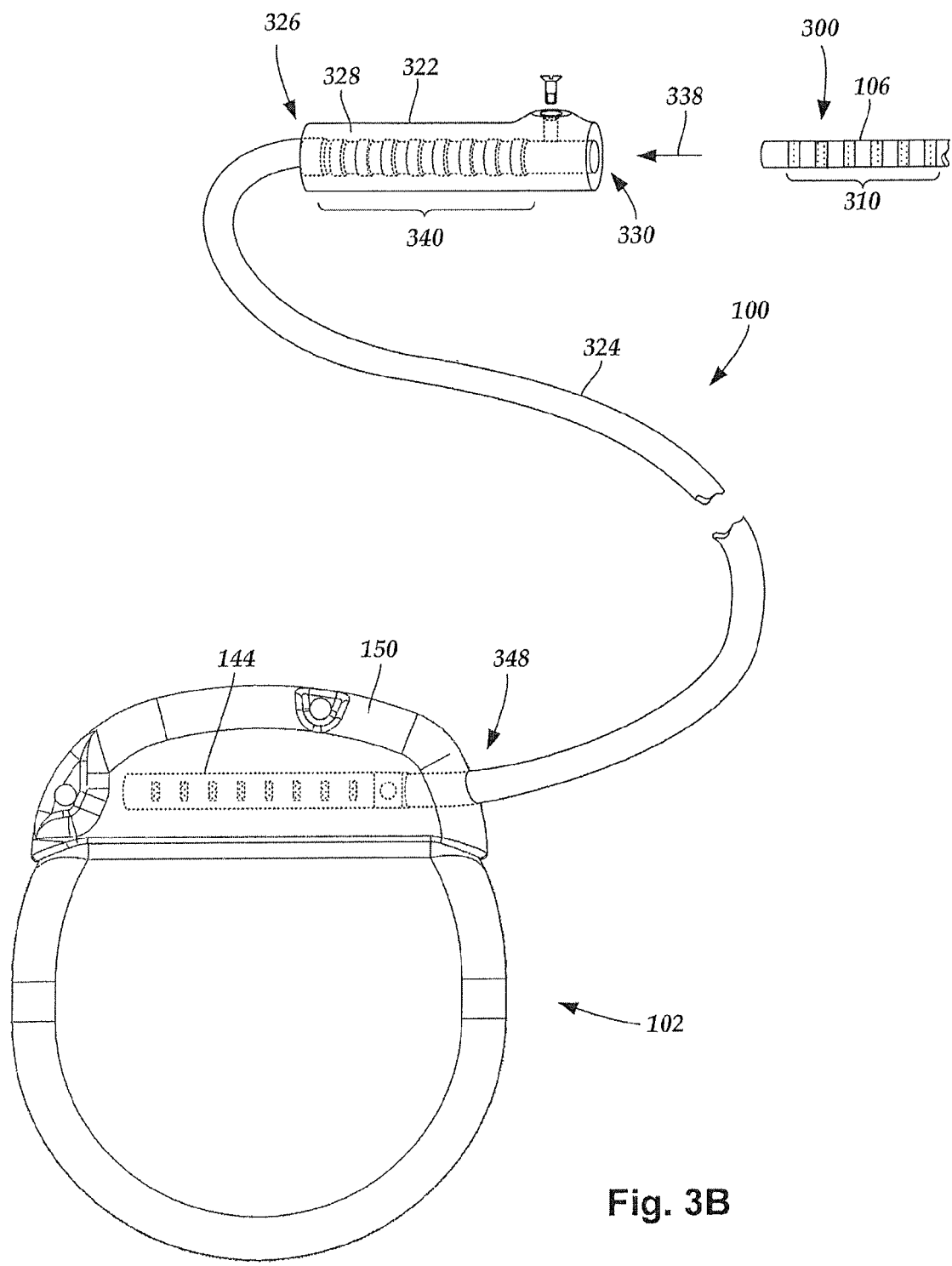
FIG. 3B is a schematic view of one embodiment of a lead extension configured and arranged to electrically couple the elongated device of FIG. 2 to the control module of FIG. 1, according to the invention.

Terminals (e.g., 310 in FIGS. 3A-3B) are typically disposed along the proximal end of the one or more lead bodies 106 of the electrical stimulation system 100 (as well as any splitters, lead extensions, adaptors, or the like) for electrical connection to corresponding connector contacts (e.g., 314 in FIGS. 3A-3B). The connector contacts are disposed in connectors (e.g., 144 in FIGS. 1-3B; and 322 FIG. 3B) which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors extend through a lumen. There may also be one or more lumens (not shown) that open at, or near, the proximal end of the one or more lead bodies 106, for example, for inserting a stylet to facilitate placement of the one or more lead bodies 106 within a body of a patient. Additionally, there may be one or more lumens (not shown) that open at, or near, the distal end of the one or more lead bodies 106, for example, for infusion of drugs or medication into the site of implantation of the one or more lead bodies 106. In at least one embodiment, the one or more lumens are flushed continually, or on a regular basis, with saline, epidural fluid, or the like. In at least some embodiments, the one or more lumens are permanently or removably sealable at the distal end.

FIG. 3A is a schematic side view of one embodiment of a proximal end of one or more elongated devices 300 configured and arranged for coupling to one embodiment of the control module connector 144. The one or more elongated devices may include, for example, one or more of the lead bodies 106 of FIG. 1, one or more intermediate devices (e.g., a splitter, the lead extension 324 of FIG. 3B, an adaptor, or the like or combinations thereof), or a combination thereof.

The control module connector 144 defines at least one port into which a proximal end of the elongated device 300 can be inserted, as shown by directional arrows 312a and 312b. In FIG. 3A (and in other figures), the connector housing 112 is shown having two ports 304a and 304b. The connector housing 112 can define any suitable number of ports including, for example, one, two, three, four, five, six, seven, eight, or more ports.

The control module connector 144 also includes a plurality of connector contacts, such as connector contact 314, disposed within each port 304a and 304b. When the elongated device 300 is inserted into the ports 304a and 304b, the connector contacts 314 can be aligned with a plurality of terminals 310 disposed along the proximal end(s) of the elongated device(s) 300 to electrically couple the control module 102 to the electrodes (134 of FIG. 1) disposed on the paddle body 104 of the lead 103. Examples of connectors in control modules are found in, for example, U.S. Pat. Nos. 7,244,150 and 8,224,450, which are incorporated by reference.

FIG. 3B is a schematic side view of another embodiment of the electrical stimulation system 100. The electrical stimulation system 100 includes a lead extension 324 that is configured and arranged to couple one or more elongated devices 300 (e.g., one of the lead bodies 106 of FIGS. 1 and 2, the splitter 207 of FIG. 2, an adaptor, another lead extension, or the like or combinations thereof) to the control module 102. In FIG. 3B, the lead extension 324 is shown coupled to a single port 304 defined in the control module connector 144. Additionally, the lead extension 324 is shown configured and arranged to couple to a single elongated device 300. In alternate embodiments, the lead extension 324 is configured and arranged to couple to multiple ports 304 defined in the control module connector 144, or to receive multiple elongated devices 300, or both.

A lead extension connector 322 is disposed on the lead extension 324. In FIG. 3B, the lead extension connector 322 is shown disposed at a distal end 326 of the lead extension 324. The lead extension connector 322 includes a connector housing 328. The connector housing 328 defines at least one port 330 into which terminals 310 of the elongated device 300 can be inserted, as shown by directional arrow 338. The connector housing 328 also includes a plurality of connector contacts, such as connector contact 340. When the elongated device 300 is inserted into the port 330, the connector contacts 340 disposed in the connector housing 328 can be aligned with the terminals 310 of the elongated device 300 to electrically couple the lead extension 324 to the electrodes (134 of FIGS. 1 and 2) disposed along the lead (103 in FIGS. 1 and 2).

In at least some embodiments, the proximal end of the lead extension 324 is similarly configured and arranged as a proximal end of the lead 103 (or other elongated device 300). The lead extension 324 may include a plurality of electrically conductive wires (not shown) that electrically couple the connector contacts 340 to a proximal end 348 of the lead extension 324 that is opposite to the distal end 326. In at least some embodiments, the conductive wires disposed in the lead extension 324 can be electrically coupled to a plurality of terminals (not shown) disposed along the proximal end 348 of the lead extension 324. In at least some embodiments, the proximal end 348 of the lead extension 324 is configured and arranged for insertion into a connector disposed in another lead extension (or another intermediate device). In other embodiments (and as shown in FIG. 3B), the proximal end 348 of the lead extension 324 is configured and arranged for insertion into the control module connector 144.

Conventional electrical stimulation systems may be potentially unsafe for use with magnetic resonance imaging ("MRI") due to the effects of electromagnetic fields in an MRI environment. A common mechanism for causing the electrical interactions between the electrical stimulation system and RF irradiation is common-mode coupling of the applied electromagnetic fields that act as a series of distributed sources along elongated conductive structures, such as leads, or conductors within leads. Common-mode induced RF currents can reach amplitudes of greater than one ampere in MRI environments. Such currents can cause heating and potentially disruptive voltages within electronic circuits.

Some of the effects of RF irradiation may include, for example, inducing current in the lead, causing undesired heating of the lead that may potentially cause tissue damage, undesired or unexpected operation of electronic components, or premature failure of electronic components. Additionally, when an electrical stimulation system is used within an MRI scanner environment, the electrical interactions between the electrical stimulation system and the MRI may cause distortions in images formed by the MRI system.

One technique for reducing common-mode coupling is to arrange the one or more conductors into a configuration that diminishes the ability for applied electromagnetic fields to couple to the conductors, or that reduces the ability of the applied electromagnetic fields to create enough heat to damage patient tissue, or both. For example, one or more of the conductors connecting at least one terminal to an electrode (or to a connector contact) can be arranged in a conductor path to eliminate or reduce the effect of RF irradiation, such as that generated during magnetic resonance imaging ("MRI"). The conductor path includes multiple units arranged in series. In some embodiments, the units are disposed along a single continuous conductor. In other embodiments, the units are separate conductive elements electrically coupled together.

Each unit includes at least three conductor segments that at least partially overlap one another to form a multi-layer region. First, each unit includes a first conductor segment that extends in a first direction along a longitudinal length of an elongated member (e.g., a lead or lead extension) from a beginning point to a first position. Second, each unit includes a second conductor segment that extends from the first position back towards (and possibly past) the beginning point to a second position. Third, each unit includes a third conductor segment that extends in the first direction from the second position to an endpoint. In at least some embodiments, the first position is between the second position and the endpoint. In at least some embodiments, the second position is between the beginning point and the first position. In at least some embodiments, the unit may include a single-layer region flanking at least one end of the multi-layer region.

The units may be electrically continuous such that the endpoint of a first unit is the beginning point of the next consecutive unit. At least one of the beginning points may be a terminal or an electrode (or connector contact). Likewise, at least one of the endpoints may be a terminal or an electrode (or connector contact). In preferred embodiments, the conductor segments are each coiled. In at least some embodiments, the conductor segments are coiled around a conductor placement sleeve. In at least some embodiments, the conductor placement sleeve defines a lumen that optionally is configured and arranged to receive a stiffening member (e.g., a stylet, or the like).

In at least some embodiments, at least one of the first, second, or third conductor segments is substantially straight.

In at least some embodiments, the first and third conductor segments are substantially straight and the second conductor segment is coiled. In at least some other embodiments, all three conductor segments are substantially straight. It will be understood that the term "substantially straight conductor segment" means that the conductor segment is not coiled. A "substantially straight conductor segment" may be curved, particularly when the lead itself is curved (see, for example, FIG. 1).

In at least some embodiments, the conductor segments are all formed from the same length of conductive material (e.g., wire or the like). The conductors may have a single filament or be multi-filar. In preferred embodiments, the conductors are multi-filar. In at least some embodiments, two or more of the conductor segments can be individual pieces of conductive material that are electrically coupled (e.g., soldered or welded) together. In at least some embodiments, a layer of insulation ("conductor insulation") is disposed over each of the conductor segments.

In at least some embodiments, the length of conductor used in the second conductor segment is at least 1.5, 1.75, 1.9, 2, 2.1, 2.25, or 2.5 times the length of either the first conductor segment or the third conductor segment. It will be recognized, however, that this ratio of conductor-segment lengths may vary among embodiments, particularly if the thickness of the conductor or thickness of the layer of conductor insulation is different for the different segments.

Figure 4:
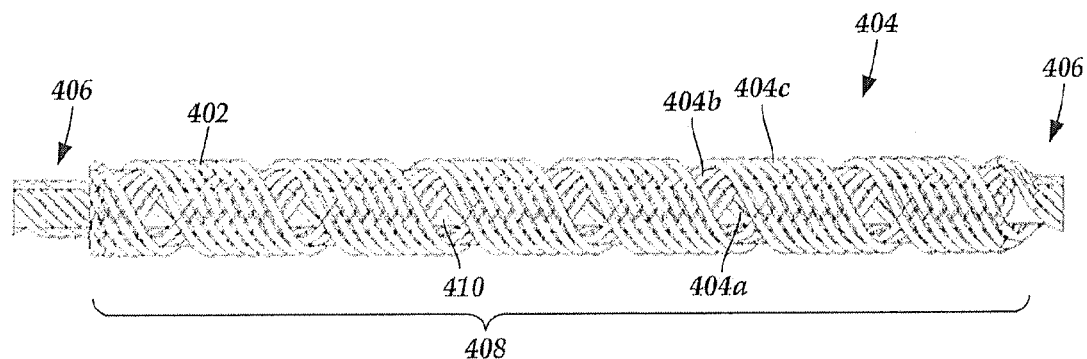
FIG. 4 is a schematic side view of one embodiment of portions of multiple conductors arranged into coiled configurations, according to the invention.

FIG. 4 schematically illustrates one embodiment of portions of multiple conductors 402. The conductors 402 are configured into multiple units, such as unit 404. Each unit includes a first conductor segment 404a, a second conductor segment 404b, and a third conductor segment 404c. In at least some embodiments, conductor insulation is disposed over the conductors 402 to electrically isolate each of the conductors 402 from one another.

Many different numbers of units may be disposed along longitudinal lengths of the conductors 402 including, for example, two, three, four, five, six, seven, eight, nine, ten, twelve, fifteen, twenty, twenty-five, thirty, forty, fifty, or more units. It will be understood that many other numbers of units may be employed as well. When a plurality of units are coupled together in series along a longitudinal length of one or more conductors, the plurality of units form a repeating series of single-layer regions, such as the single-layer regions 406, separated from one another by a multi-layer region, such as the multi-layer region 408.

In at least some embodiments, the conductors 402 are disposed along a conductor placement sleeve 410. The conductor placement sleeve 410 can be formed from any suitable biocompatible material including, for example, one or more polymers. In at least some embodiments, conductor insulation is disposed over the conductors 402 to encapsulate the conductors 402 and electrically isolate the conductors 402 from one another.

In at least some embodiments, one or more conductors having one or more units may be disposed in an elongated member (e.g., a lead or lead extension). In at least some embodiments, the ends of the conductors 402 can be coupled to terminals, electrodes, or connector contacts. In preferred embodiments, each of the conductors in an elongated member is configured into units. In at least some embodiments, only a subset of the conductors disposed in an elongated member includes one or more units, the remaining conductors having a different arrangement (for example, a single conductor segment between the terminal(s) and electrode(s)/connector contact(s)).

When one or more conductors are disposed along a lead body (or lead extension body), the arrangement of the conductor(s) may cause one or more open spaces to be formed along a longitudinal length of the lead body. For example, in the case of conductors arranged into coiled configurations (e.g., one or more of the above-described units, or the like), the lead may include one or more open spaces formed between two or more conductors, between two or more units of the same conductor (e.g., single layer regions 406), between two or more conductor segments of the same unit (e.g., between layers of coils), or between one or more portions of the same conductor segment (e.g., between individual coils).

Figure 6A:
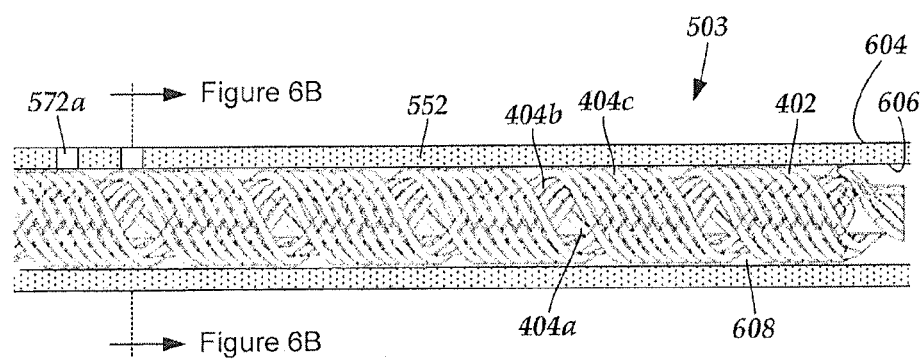
FIG. 6A is a schematic longitudinal cross-sectional view of one embodiment of a portion of the jacket of FIG. 5 rotated ninety degrees and disposed over a side view of the conductor portions of FIG. 4, the jacket defining apertures extending completely through the jacket, according to the invention.
Figure 6B:
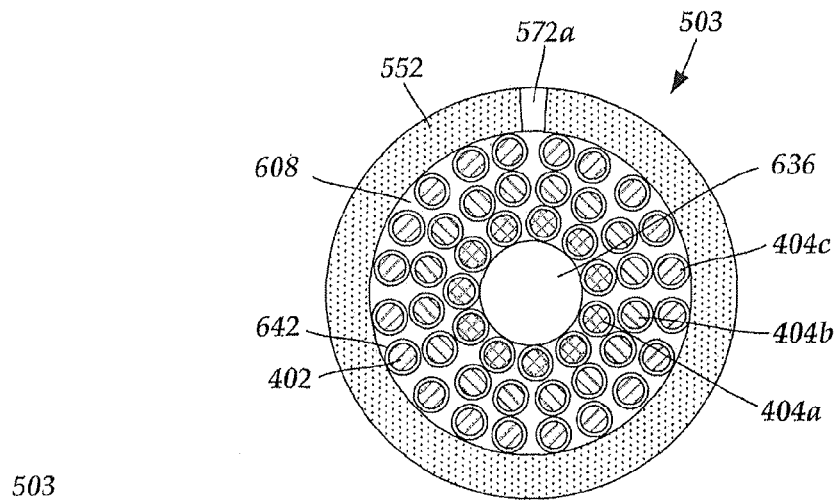
FIG. 6B is a schematic transverse cross-sectional view of one embodiment of the jacket portion of FIG. 6A disposed over the conductor portions of FIG. 6A, according to the invention.
Figure 6C:
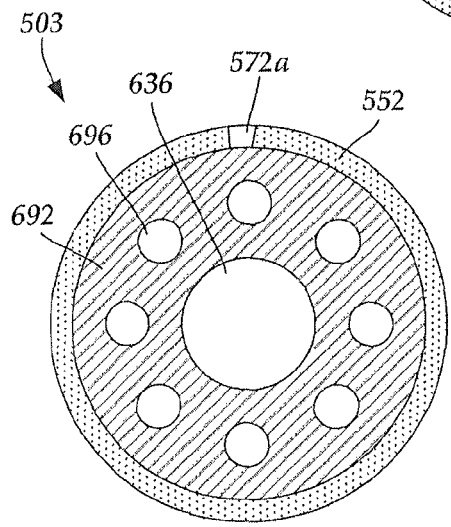
FIG. 6C is a transverse cross-sectional view of one embodiment of a portion of the lead of FIG. 5, the lead including a multi-lumen conductor guide and a plurality of conductor lumens, according to the invention.
Figure 6D:
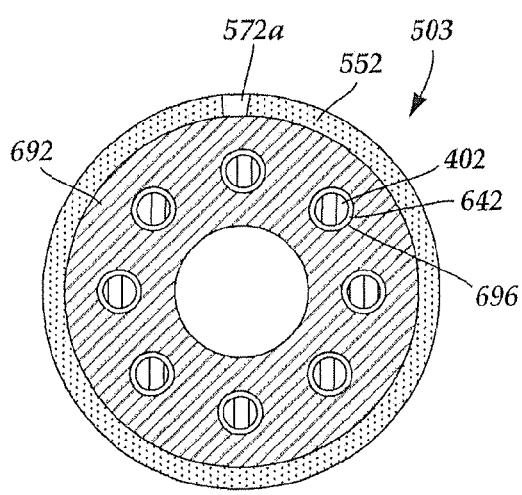
FIG. 6D is a transverse cross-sectional view of one embodiment of conductors disposed in each of a plurality of conductor lumens of the multi-lumen conductor guide of FIG. 6C, according to the invention.

It will be understood that open spaces may be formed along leads with conductors arranged into substantially-straight configurations, as well (see e.g., FIGS. 6C-6D). Open spaces may be formed, for example, between two or more conductors, between electrodes and adjacent spacers, between terminals and adjacent spacers, within conductor lumens defined along the lead body (see e.g., FIGS. 6C-6D), or the like.

Figure 5:
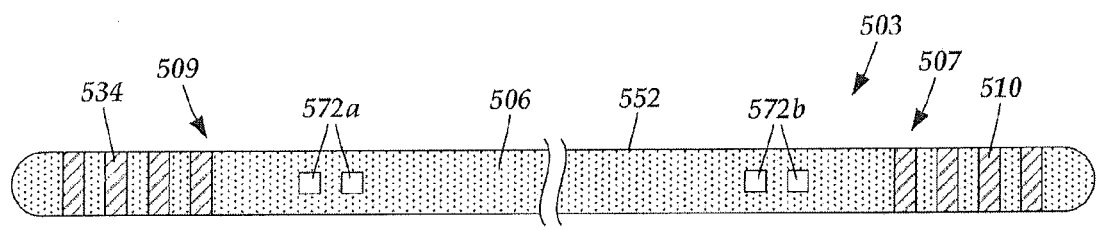
FIG. 5 is a schematic side view of one embodiment of a percutaneous lead with a jacket forming an outer surface of the lead, the jacket defining apertures along each of a distal end portion of the lead and along a proximal end portion of the lead, according to the invention.

Turning to FIG. 5, when a lead is implanted in a patient, one or more of the electromagnetic properties of the lead (e.g., the conductivity, permittivity, or the like) may change over time. As described below, these changes over time to the electromagnetic properties of the lead may be due, at least in part, to the presence of open spaces within the lead.

In many instances, implanted leads are disposed in fluid-containing portions of the patient. Conventional leads may include a body that is covered by an outer member (e.g., a jacket) that substantially prevents fluids (e.g., bodily fluids, introduced fluids, fluid vapor, or the like) in the local external environment from entering the lead. Over time, however, at least some fluid often seeps into the lead and at least partially fills in open spaces. As fluid displaces air in the open spaces, one or more electromagnetic properties (e.g., permittivity, conductivity, or the like) within portions of the lead may begin to change over time such that portions of the lead with air in the open spaces have different electromagnetic properties from portions of the lead without fluid in the open spaces.

Such changes to the electromagnetic properties within different portions of the lead can potentially cause a change in performance of the lead. For example, changes to the electromagnetic properties of the lead may amplify the ability for applied electromagnetic fields to couple to the conductors during exposure to certain RF energy (e.g., during performance of an MRI procedure), or increase the ability of the applied electromagnetic fields to create enough heat to damage patient tissue, or both, thereby reducing the performance of the lead during these conditions. In some cases, changes in performance may also include a diminished efficacy of stimulation (e.g., overstimulation, understimulation, unpredictable or uncontrollable stimulation, or the like or combinations thereof), or even a complete loss of efficacy of stimulation.

Despite much effort put forth by lead designers to create water-tight jackets, during lead operation at least some fluid from a local implantation environment will often eventually seep into the lead via, for example, manufacturing defects, broken seams or joints, broken-down lead materials, or the like. Unfortunately, since such seepage is typically not planned for, the actual rate and extent of seepage of the fluid into the lead is not known at the time of implantation and may not be controllable during lead operation.

One way to promote consistent performance of the lead is to facilitate fluid ingress into the lead to displace open spaces in the lead with fluid. Predictably bringing the lead to a fluid equilibrium may reduce the magnitude of potential change in performance of the lead as a result of exposure to RF energy.

Facilitating fluid ingress into the lead may include modulating at least one of the rate of fluid ingress into the lead or the extent of fluid ingress into the lead. In at least some embodiments, fluid ingress into the lead is promoted by defining one or more apertures (e.g., pores, perforations, fenestrations, holes, slits, slots, gaps, punctures, clefts, cracks, fissures, orifices, or the like) in the lead that extend completely through an outer covering of the lead to an interior portion of the lead. The one or more apertures enable fluid from a local environment exterior to the lead to into the lead body.

It will be understood that patient tissue is stimulated via the one or more electrodes 534. In preferred embodiments, the fluid input to the lead 503 displaces air-filled open spaces within the lead 503, and is not intended to directly contact conductors disposed within the lead body 506 and is not intended to form accessory conduction pathways along the lead 503.

FIG. 5 is a schematic side view of one embodiment of a lead 503. The lead 503 includes a lead body 506 with a proximal end portion 507 and a distal end portion 509. A plurality of terminals 510 are disposed along the proximal end portion 507 of the lead body 506, and a plurality of electrodes 534 are disposed along the distal end portion 509 of the lead body 506. The lead 403 includes a jacket 552 forming an outer surface along at least a portion of the lead 503. One or more first apertures 572*a* and one or more second apertures 572*b* are defined along the jacket 552 and extend therethrough to an interior of the lead body 506. Examples of lead jackets with apertures are found in, for example, U.S. patent application Ser. No. 13/962,282, which is incorporated by reference.

In at least some embodiments, the jacket 552 extends an entire longitudinal length of the lead 503. In other embodiments, the jacket 552 extends less than the entire longitudinal length of the lead 503. In at least some embodiments, the jacket 552 extends from the proximal-most electrode of the plurality of electrodes 534 to the distal-most terminal of the plurality of terminals 510.

The apertures 572*a* and 572*b* can be defined at any suitable location along a longitudinal length of the lead body 506. In at least some embodiments, at least one first aperture 572*a* or at least one second aperture 572*b* is defined along the proximal end portion 507 of the lead body 506. In at least some embodiments, at least one first aperture 572*a* or at least one second aperture 572*b* is defined along the distal end portion 509 of the lead body 506. In at least some embodiments, at least one first aperture 572*a* or at least one second aperture 572*b* is defined along the proximal end portion 507 of the lead body 506 and the other of the at least one first aperture 572*a* or the at least one second aperture 572*b* is defined along the distal end portion 509 of the lead body 506.

In FIG. 5 (and in other figures), the first apertures 572*a* are shown disposed along the distal end portion 509 of the lead body 506 and the second apertures 572*b* are shown disposed along the proximal end portion 507 of the lead body 506. This arrangement is intended for clarity of explanation and is not intended to be limiting. As mentioned above, the first apertures 572*a* and the second apertures 572*b* can be defined at any suitable location along the longitudinal length of the lead body 506.

FIG. 6A is a schematic view of one embodiment of a section of the lead 503 that includes the first apertures 572*a*. FIG. 6B is a schematic transverse cross-sectional view of one embodiment of the lead 503 along the section of the lead 503 shown in FIG. 6A. The lead 503 shown in FIGS. 6A-6B includes the jacket 552 disposed over the conductor portions 402.

In FIGS. 6A-6B, the portions of the conductors 402 shown are disposed in one embodiment of a coiled configuration where the conductors 402 are configured into a plurality of units disposed over a stylet lumen 636, as shown in FIG. 4. It will be understood that this is one of many possible conductor configurations, and is not intended as being limiting. It will be understood that the conductors 402 can be arranged in any suitable configuration along the lead including, for example, configured into one or more of the above-described units, coiled, partially-coiled, straight, partially-straight, overlapped, non-overlapped, partially-overlapped, jumbled, tangled, or the like or combinations thereof. Conductor insulation 642 is shown disposed over the conductors 402 to electrically isolate each of the conductors 402 from one another. As shown in FIGS. 6A-6B, the conductors 402 are arranged such that one or more open spaces, such as open space 608, are formed along a length of the lead 503.

FIGS. 6C-6D show an alternate conductor configuration, where substantially-straight conductors are disposed in conductor lumens formed along a multi-lumen conductor guide. In FIG. 6C, the lead 503 is shown having an elongated multi-lumen conductor guide 692. The multi-lumen conductor guide 692 defines the stylet lumen 636 and a plurality of conductor lumens, such as conductor lumen 696. In FIG. 6C, the conductor lumens 696 are shown disposed around the stylet lumen 696. In FIG. 6D, the conductors 402 are shown disposed in the conductor lumens 696. The multi-lumen conductor guide 692 may extend all, or one or more portions, of the longitudinal length of the lead 503 from the electrodes 534 to the terminals 510. The conductor lumens 696 can have any suitable cross-sectional shape (e.g., round, oval, rectangular, triangular, or the like).

As shown in FIGS. 6C-6D, the jacket 552 has an outer surface 604 and an inner surface 606. In at least some embodiments, the outer surface 604 of the jacket 552 forms an outer surface of the lead 503. Optionally, one or more layers of coatings, or annealing materials, or both, may be disposed over at least a portion of the outer surface 604 of the jacket 552. In at least some embodiments, the inner surface 606 of the jacket 552 is open to the conductors 402. The jacket 552 can have any suitable thickness. It will be understood that the thickness of the jacket 552 shown in FIGS. 6A-6D is meant to illustrate one embodiment and is dimensioned primarily for clarity of illustration. The thickness of the jacket 652 in relation to a diameter of the lead 503 can be either larger or smaller from what is shown in FIGS. 6A-6D.

Figure 7:
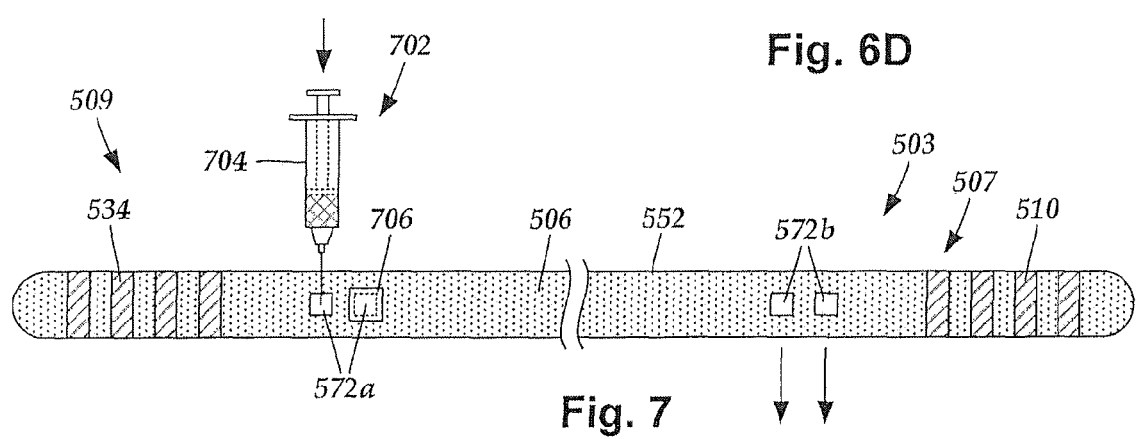
FIG. 7 is a schematic side view of one embodiment of a fluid-insertion assembly and a portion of the lead of FIG. 5, the fluid-insertion assembly including a syringe inserted into an aperture defined along the lead, according to the invention.

Turning to FIG. 7, as discussed above displacement of air from the open spaces in the lead may reduce differences in one or more electromagnetic properties (e.g., permittivity, conductivity, or the like). Over time after lead implantation, an electrical equilibrium is reached between the open spaces in the lead and the local environment external to the lead. In at least some embodiments, as the differences in electromagnetic properties between the lead and the local environment are reduced the performance of the lead during exposure to RF irradiation (e.g., during an MRI procedure) improves as the lead performance becomes more consistent and predictable. Accordingly, it may be advantageous for the implanted lead to be at, or near, electrical equilibrium prior to the patient undergoing an MRI procedure to improve lead performance during the MRI procedure.

Once the lead is implanted, fluid from a local environment exterior to the lead jacket (e.g., fluid from the target stimulation location) may pass through the jacket 552 and into the lead body 506. In which case, the fluid may be one or more bodily fluids (e.g., blood, cerebrospinal fluid, mucous, bile, chyle, lymph fluid, gastric juice, pleural fluid, peritoneal fluid, cerumen, or the like or combinations thereof).

It may be advantageous for the lead 503 to be at least partially filled with one or more fluids prior to implantation (e.g., pre-soaked) in order to reduce the amount of time needed after implantation for the lead to reach an electrical equilibrium with the local environment at the target stimulation location. It will be understood that such electrical equilibrium may occur when the lead is less than completely filled.

As herein described, systems and methods for inputting fluid into the lead, prior to implantation, are described. In at least some embodiments, fluid is passively input to the lead. For example, in at least some embodiments fluid ingress into the lead may be facilitated by submerging the lead in a reservoir filled with fluid. Alternately, in at least some embodiments fluid is actively pumped into the lead. For example, in at least some embodiments a fluid-insertion assembly is used to facilitate fluid ingress into the lead. Facilitating fluid ingress into the lead may include modulating at least one of the rate of fluid ingress into the lead or the extent of fluid ingress into the lead.

Figure 8:
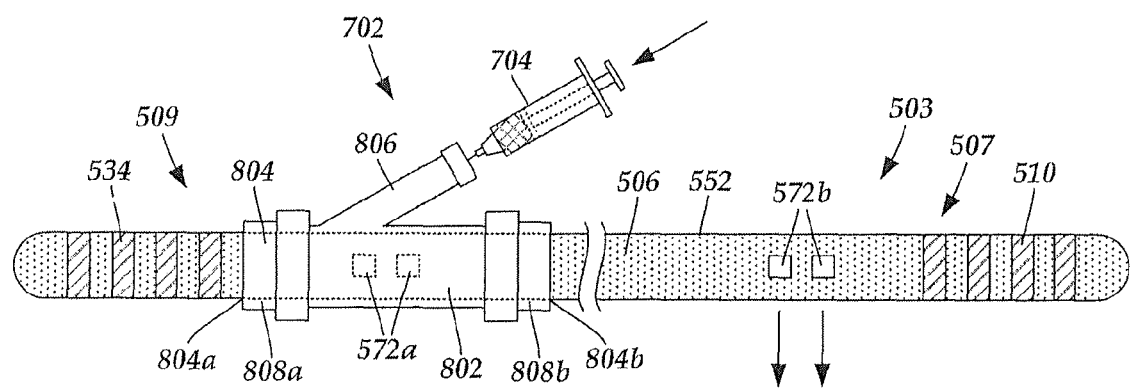
FIG. 8 is a schematic side view of a second embodiment of a fluid-insertion assembly and a portion of the lead of FIG. 5, the fluid-insertion assembly including a sealed mounting body disposed over one or more apertures defined along a portion of the lead and a port for receiving a syringe for imputing fluid into the lead via the sealed mounting body, according to the invention.
Figure 9:
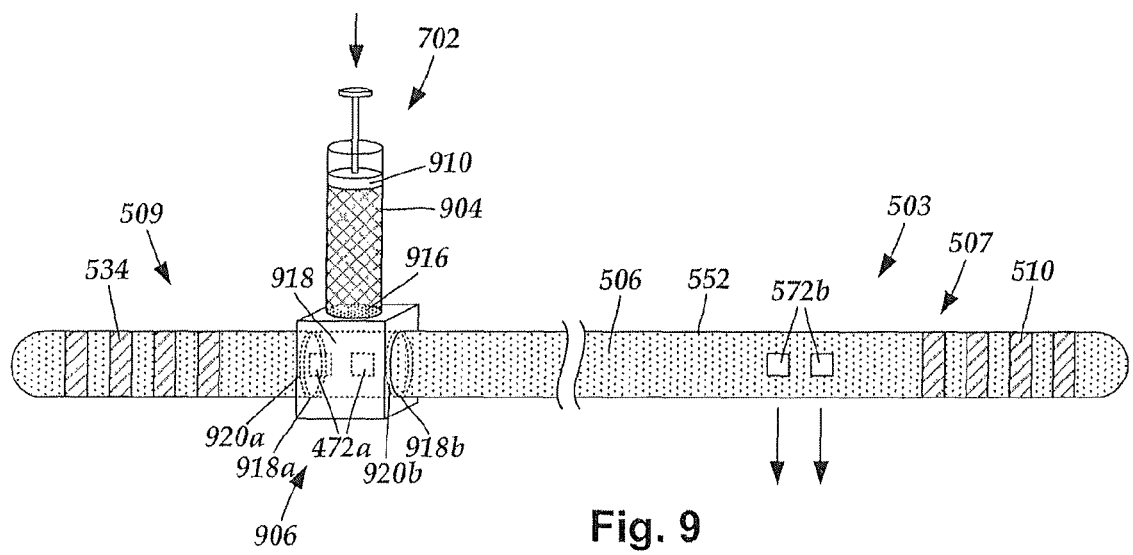
FIG. 9 is a schematic side view of a third embodiment of a fluid-insertion assembly and a portion of the lead of FIG. 5, the fluid-insertion assembly including a sealed mounting body disposed over one or more apertures defined along a portion of the lead, a fluid reservoir coupled to the mounting body, and a piston for urging fluid from the fluid reservoir into the lead via the sealed mounting body, according to the invention.

FIGS. 7-9 schematically illustrate several different embodiments of fluid-insertion assemblies suitable for use to facilitate fluid ingress into the lead. Any suitable fluid may be input into the lead that provides similar, or even identical, lead performance as would be achieved if the lead were filled with interstitial fluid from the target stimulation location.

In at least some embodiments, the input fluid is a liquid. In at least some embodiments, the input fluid has a dielectric constant equal to a dielectric constant of bodily fluid in the local environment at a target stimulation location within which the lead is implanted. In at least some embodiments, the input fluid has a pH equal to a pH of bodily fluid in the local environment at the target stimulation location. In at least some embodiments, the input fluid has conductivity equal to conductivity of bodily fluid in the local environment at the target stimulation location. In at least some embodiments, the input fluid has a permittivity equal to a permittivity of bodily fluid in the local environment at the target stimulation location. In at least some embodiments, the input fluid is water-based. In at least some embodiments, the input fluid is a saline solution. In at least some embodiments, the input fluid is bodily fluid extracted from the target implantation location.

FIG. 7 is a schematic side view of one embodiment of a fluid-insertion assembly 702 and the lead 503. The fluid-insertion assembly 702 includes a syringe 704 configured to input fluid into the one or more first apertures 572a. Alternately, a pump, a piston, or the like, may be adapted for insertion into one or more of the first apertures 572a and used in lieu of a syringe 704. In at least some embodiments, one or more hoses may be used to couple the pump, piston, or the like, to a needle configured for insertion into one or more of the first apertures 572a.

The syringe 704 may include a barrel, which may form an enclosure to house the fluid. The syringe 704 may include a discharge plunger at a first end of the barrel. The discharge plunger may be pressed to urge fluid out of the syringe 704, via a needle disposed at a second end of the barrel. The rate and amount of fluid urged out of the syringe 704 may depend upon the pressure applied on the discharge plunger. The rate and amount of the fluid ingress into the aperture 472a may also depend upon the diameter of the needle. The syringe 704 can be made of any suitable material including, for example, plastic, glass, or the like. In some embodiments, the piston 910 is configured and arranged for being manually pressed by a user of the fluid-insertion assembly 702. In other embodiments, the piston 910 is pressed using an automated system.

It will be understood that in FIG. 7 (and in other figures) the first apertures 572a and the second apertures 572b can be defined along any suitable portion of the lead 503. In at least some embodiments, the first apertures 572a and the second apertures 572b are defined along opposing end portions of the lead 503. In some embodiments, the first apertures 572a are defined along the distal end portion 509 and the second apertures 572b are defined along the proximal end portion 507. In other embodiments, the first apertures 572a are defined along the proximal end portion 507 and the second apertures 572b are defined along the distal end portion 509.

Any suitable amount of fluid may be input to the lead 503. In at least some embodiments, fluid is input to the lead 503 until some time after the fluid begins to flow out of one or more of the second apertures 572b. The distance between the first apertures 572a and the second apertures 572b along the longitudinal length of the lead body 506 may influence the degree of filling of the lead 503 with fluid prior to lead implantation. It may be advantageous to define the apertures 572a and 572b at opposing end portions of the lead body 506 so that, when fluid is input to the lead 503 via the one or more first apertures 572a, the fluid crosses substantially the entire longitudinal length of the lead body 506 before reaching one or more of the second apertures 572b. In which case, the lead 503 may become more filled with fluid prior to implantation than if the first apertures 572a and the second apertures 572b are defined in proximity to one another along the longitudinal length of the lead 503.

Optionally, the fluid-insertion assembly 702 includes one or more aperture covers 706 configured for temporarily disposing over one or more apertures to temporarily reduce, or even temporarily prevent, input fluid from leaking from the lead. In at least some embodiments, the one or more aperture covers 706 may be disposed over one or more apertures defined along the same (or the opposing) end portion 507 or 509 of the lead body 506 as the one or more apertures within which the fluid-insertion assembly is disposed.

FIG. 8 is a schematic side view of a second embodiment of the fluid-insertion assembly 702 disposed along a portion of the lead 503. The fluid-insertion assembly 702 shown in FIG. 8 includes a mounting body 802 disposed over one or more of the first apertures 572a. The mounting body 802 is configured and arranged to couple the fluid-insertion assembly 702 to the jacket 552 such that the mounting body 802 forms a watertight seal around at least one of the first apertures 572a. In at least some embodiments, the mounting body 802 is formed as a tube-shaped, or substantially-tube-shaped, structure. In at least some embodiments, the mounting body 802 is configured and arranged for sliding over one end of the lead 503. In at least some embodiments, the mounting body 802 defines a mounting aperture 804 that includes a first end portion 804a and a second end portion 804b.

The mounting body 802 includes a first lead-aperture seal 808a disposed along the first end portion 804a, and a second lead-aperture seal 808b disposed along the second end portion 804b. The lead-aperture seals 808a and 808b provide a watertight seal along the end portions of the mounting body 802, thereby forming a space formed between a portion of the jacket 552 that defines at least one first aperture 572a, the mounting body 802, the first lead-aperture seal 808a, and the second lead-aperture seal 808b.

A fluid-input port 806 is in fluid communication with the watertight space. In at least some embodiments, the fluid input port 806 and the mounting body 802 collectively form a Y-shaped, or T-shaped, structure. When the mounting body 802 is disposed over the one or more first apertures 572a, the fluid-input port 806 is configured and arranged for receiving fluid for inputting into the lead via the first apertures 572a. In at least some embodiments, the fluid-input port 806 is configured and arranged to receive a fluid-input device, such as the syringe 704, for imputing fluid into the fluid-input port 806.

In at least some embodiments, the lead-aperture seals 808a and 808b have adjustable valves. The valves may be structured in a manner that the lead 503 can be made to easily pass through the valve when the valve is untightened. Then, once the lead 503 is securely placed, the valves can be tightened to seal the ends of the mounting body 802. In at least some embodiments, the seals may include one or more Tuohy-Borst seals to seal the mounting body 802.

The mounting body 802 and the lead-aperture seals 808a and 808b may be made up of any suitable material like polycarbonate. The valve can be made of any suitable material that may be an elastomeric. Examples of elastomeric materials may include silicone. When the jacket 552 and the valve are both formed from silicone, the silicone valve may temporarily stick to the jacket 552, thereby forming a watertight seal.

FIG. 9 is a schematic side view of a third embodiment of a fluid-insertion assembly 702 disposed along a portion of the lead 503. The fluid-insertion assembly 702 shown in FIG. 9 includes a fluid reservoir 904 coupled to a mounting body 906. In FIG. 9, the mounting body 906 is shown disposed over the first apertures 572a.

The mounting body 906 is configured and arranged to couple the fluid-insertion assembly 702 to the jacket 552 such that the mounting body 906 forms a watertight seal around at least one of the first apertures 572a. In at least some embodiments, the mounting body 906 is configured and arranged for sliding over one end of the lead 503. In at least some embodiments, the mounting body 906 defines a mounting aperture 918 that includes a first end portion 918a and a second end portion 918b.

The mounting body 906 includes a first lead-aperture seal 920a disposed along the first end portion 918a, and a second lead-aperture seal 920b disposed along the second end portion 918b. The lead-aperture seals 920a and 920b provide a watertight seal along the end portions of the mounting body 906, thereby forming a space between a portion of the jacket 552 that defines at least one first aperture 572a, the mounting body 906, the first lead-aperture seal 920a, and the second lead-aperture seal 920b.

The fluid reservoir 904 is in fluid communication with the watertight space. In at least some embodiments, a septum 916 is disposed between the fluid reservoir 904 and the mounting body 906 to reduce, or even prevent, unprovoked movement of fluid between the fluid reservoir 904 and the mounting body 906. The septum 916 may be defined as a membrane.

When the mounting body 906 is disposed over the one or more first apertures 572a, the fluid reservoir 904 is configured and arranged for inputting fluid into the lead 503 via the one or more first apertures 572a over which the fluid-insertion assembly 702 is disposed. The fluid reservoir may have an adjustable volume. For example, in at least some embodiments the fluid-insertion assembly 702 further includes a piston 910 for urging fluid from the fluid reservoir 904. The piston 910 may be configured and arranged for being manually pressed by a user of the fluid-insertion assembly 702. In other embodiments, the piston 910 is pressed using an automated system. Alternately, or in lieu of using the piston 910, the volume of the fluid reservoir 904 may be adjusted by squeezing (or otherwise compressing) the fluid reservoir 904 to urge fluid from the fluid reservoir 904 into the lead 503. In some embodiments, the fluid reservoir 904 is refillable. In other embodiments, the fluid reservoir 904 is configured and arranged for single use.

In at least some embodiments, the lead-aperture seals 920a and 920b have adjustable valves. The valves may be structured in a manner that the lead 503 can be made to easily pass through the valve when the valve is untightened. Then, once the lead 503 is securely placed, the valves can be tightened to seal the ends of the mounting body 906. In at least some embodiments, the seals may include one or more Tuohy-Borst seals to seal the mounting body 906.

The mounting body 906 and the lead-aperture seals 920a and 920b may be made up of any suitable material like polycarbonate. The valve can be made of any suitable material that may be an elastomeric. Examples of elastomeric materials may include silicone. When the jacket 552 and the valve are both formed from silicone, the silicone valve may temporarily stick to the jacket 552, thereby forming a watertight seal.

With respect to each of the fluid-insertion assemblies shown in FIGS. 7-9, as discussed above fluid may be input to the first apertures 572a until some time after fluid begins exiting the second apertures 572b. Alternately, the amount of fluid input to the lead may be based on a particular volume of fluid. For example, the amount of fluid input to the lead may be based on an estimated collective volume of open space defined in the lead 503. In at least some embodiments, the amount of fluid input to the lead is equal to an estimated amount of open space in the lead 503. In at least some embodiments, the amount of fluid input to the lead is greater than an estimated amount of open space in the lead 503. In at least some embodiments, the amount of fluid input to the lead is less than an estimated amount of open space in the lead 503.

In at least some embodiments, the amount of fluid input to the lead is no greater than 50%, 40%, 30%, 20%, 10%, 5% of the overall volume of the lead 503. In at least some embodiments, the amount of fluid input to the lead is no less than 5%, 10%, 20%, 30%, 40%, 50% of the overall volume of the lead 503. In at least some embodiments, the amount of fluid input to the lead is no greater than 50% and no less than 5% of the overall volume of the lead 503. In at least some embodiments, the amount of fluid input to the lead is no greater than 40% and no less than 5% of the overall volume of the lead 503. In at least some embodiments, the amount of fluid input to the lead is no greater than 30% and no less than 5% of the overall volume of the lead 503. In at least some embodiments, the amount of fluid input to the lead is no greater than 20% and no less than 5% of the overall volume of the lead 503.

In at least some embodiments, fluid is input into the lead 503, using the fluid-insertion assembly 702, until an electrical equilibrium is reached. In at least some embodiments, fluid is input into the lead 503, using the fluid-insertion assembly 702, until the lead 303 is filled completely. In at least some embodiments, fluid is input to the lead 503 using the fluid-insertion assembly 702, until at least 30%, 40%, 50%, 55%, 60%, 65%, 70%, 75%, 80%, 85%, 90%, 95%, 96%, 97%, 98%, or 99%, or more of the combined open space within the lead is filled with fluid. It will be understood that the above percentages of open spaces within the lead do not include open space within the stylet lumen (see e.g., 636 in FIG. 6B) which may be sealed from fluid ingress.

After the lead 503 is pre-soaked, the lead 503 may be inserted into the body of the patient and advanced to the target stimulation location. In some embodiments, fluid egress from the lead is reduced, or even prevented, during implantation by temporarily covering one or more of the first apertures 572a, or one or more of the second apertures 572b, or both, or by water tension, or the like or combinations thereof. In other embodiments, fluid egress is allowed to continue unhindered during lead implantation.

The amount of time needed for the lead to reach an electrical equilibrium after fluid is input to the lead and the lead is advanced to the target stimulation location may vary. In at least some embodiments, the lead is at an electrical equilibrium with the local environment at the target stimulation location at the time of implantation. In at least some embodiments, the lead is at an electrical equilibrium with the local environment at the target stimulation location within no more than twenty, eighteen, sixteen, fourteen, twelve, ten, nine, eight, seven, six, five, four, three, or two days from the time of implantation.

Figure 10:
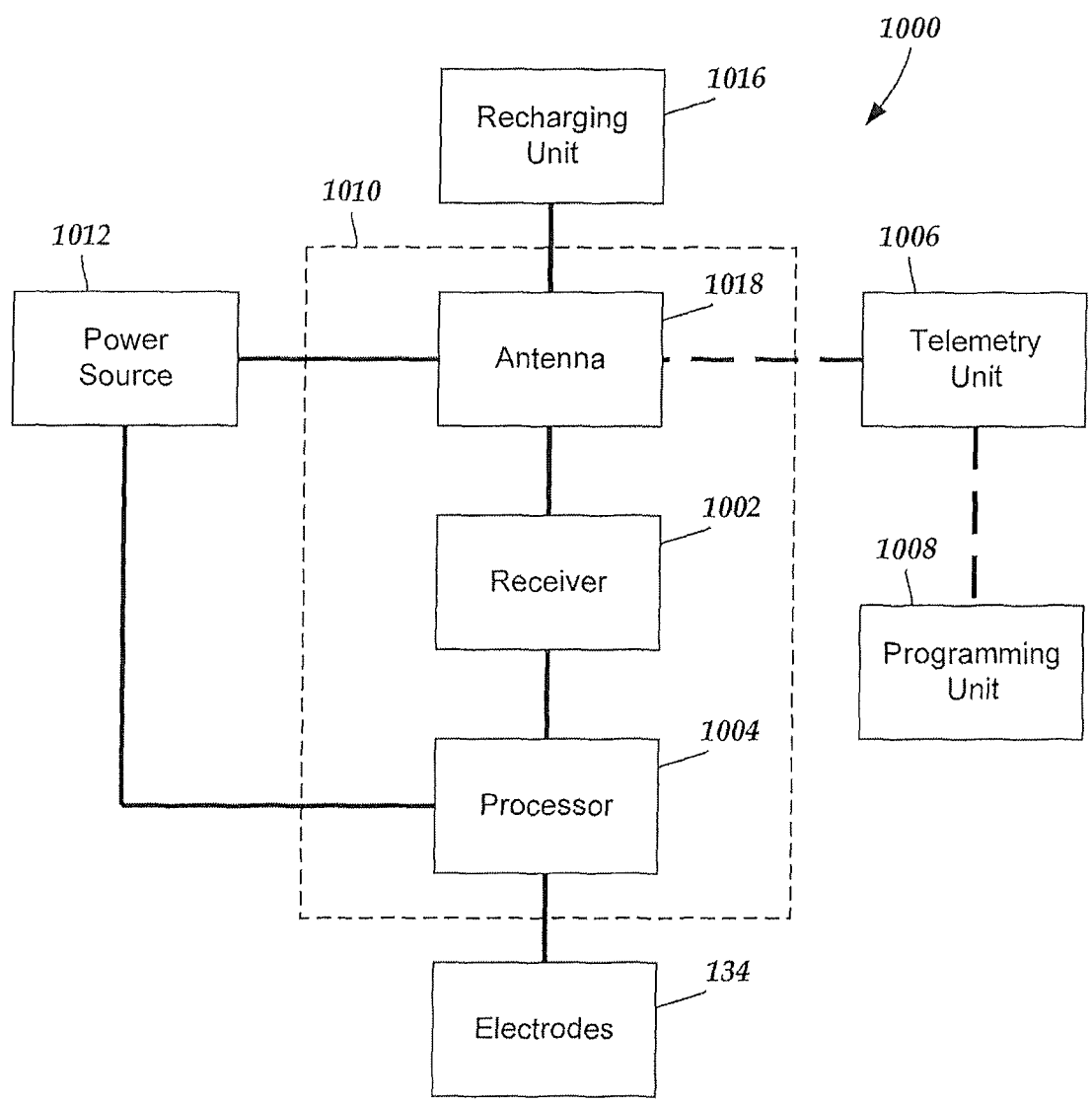
FIG. 10 is a schematic overview of one embodiment of components of a stimulation system, including an electronic subassembly disposed within a control module, according to the invention.

FIG. 10 is a schematic overview of one embodiment of components of an electrical stimulation system 1000 including an electronic subassembly 1010 disposed within a control module. It will be understood that the electrical stimulation system can include more, fewer, or different components and can have a variety of different configurations including those configurations disclosed in the stimulator references cited herein.

Some of the components (for example, a power source 1012, an antenna 1018, a receiver 1002, and a processor 1004) of the electrical stimulation system can be positioned on one or more circuit boards or similar carriers within a sealed housing of an implantable pulse generator, if desired. Any power source 1012 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via the optional antenna 1018 or a secondary antenna. The external power source can be in a device that is mounted on the skin of the user or in a unit that is provided near the user on a permanent or periodic basis.

If the power source 1012 is a rechargeable battery, the battery may be recharged using the optional antenna 1018, if desired. Power can be provided to the battery for recharging by inductively coupling the battery through the antenna to a recharging unit 1016 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. The processor 1004 is generally included to control the timing and electrical characteristics of the electrical stimulation system. For example, the processor 1004 can, if desired, control one or more of the timing, frequency, strength, duration, and waveform of the pulses. In addition, the processor 1004 can select which electrodes can be used to provide stimulation, if desired. In some embodiments, the processor 1004 selects which electrode(s) are cathodes and which electrode(s) are anodes. In some embodiments, the processor 1004 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1008 that, for example, allows modification of pulse characteristics. In the illustrated embodiment, the processor 1004 is coupled to a receiver 1002 which, in turn, is coupled to the optional antenna 1018. This allows the processor 1004 to receive instructions from an external source to, for example, direct the pulse characteristics and the selection of electrodes, if desired.

In one embodiment, the antenna 1018 is capable of receiving signals (e.g., RF signals) from an external telemetry unit 1006 which is programmed by the programming unit 1008. The programming unit 1008 can be external to, or part of, the telemetry unit 1006. The telemetry unit 1006 can be a device that is worn on the skin of the user or can be carried by the user and can have a form similar to a pager, cellular phone, or remote control, if desired. As another alternative, the telemetry unit 1006 may not be worn or carried by the user but may only be available at a home station or at a clinician's office. The programming unit 1008 can be any unit that can provide information to the telemetry unit 1006 for transmission to the electrical stimulation system 1000. The programming unit 1008 can be part of the telemetry unit 1006 or can provide signals or information to the telemetry unit 1006 via a wireless or wired connection. One example of a suitable programming unit is a computer operated by the user or clinician to send signals to the telemetry unit 1006.

The signals sent to the processor 1004 via the antenna 1018 and the receiver 1002 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1000 to cease operation, to start operation, to start charging the battery, or to stop charging the battery. In other embodiments, the stimulation system does not include the antenna 1018 or receiver 1002 and the processor 1004 operates as programmed.

Optionally, the electrical stimulation system 1000 may include a transmitter (not shown) coupled to the processor 1004 and the antenna 1018 for transmitting signals back to the telemetry unit 1006 or another unit capable of receiving the signals. For example, the electrical stimulation system 1000 may transmit signals indicating whether the electrical stimulation system 1000 is operating properly or not or indicating when the battery needs to be charged or the level of charge remaining in the battery. The processor 1004 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An insertion kit for an electrical stimulation system, the insertion kit comprising:
    a lead configured and arranged for insertion into a patient, the lead comprising
        a lead body having a distal end portion, a proximal end portion, and a longitudinal length,
        a jacket disposed over at least a portion of the longitudinal length of the lead body, the jacket having an outer surface and an opposing inner surface, at least a portion of the outer surface of the jacket forming at least a portion of an outer surface of the lead body, at least a portion of the inner surface of the jacket open to the lead body,
        a plurality of apertures defined along the outer surface of the lead body with each of the plurality of apertures extending completely through the jacket to the inner surface, the plurality of apertures comprising at least one first aperture,
        a plurality of electrodes disposed along the distal end portion of the lead body,
        a plurality of terminals disposed along the proximal end portion of the lead body,
        a plurality of conductors electrically coupling the plurality of electrodes to the plurality of terminals, and
        conductor insulation disposed over each of the plurality of conductors,
        wherein at least a portion of the conductor insulation is in fluid communication with the local environment external to the lead via the plurality of apertures; and
    a fluid-insertion assembly configured and arranged for inputting fluid into the lead, via the at least one first aperture, prior to implantation of the lead into the patient, wherein the fluid-insertion assembly is configured and arranged for disposing over a portion of the jacket to completely cover the at least one first aperture.

2. The insertion kit of claim 1, wherein the at least one first aperture is defined along one of the distal end portion or the proximal end portion of the lead body.

3. The insertion kit of claim 1 wherein the fluid-insertion assembly is configured and arranged for inputting fluid into the lead to facilitate reaching an electrical equilibrium between the lead and interstitial fluid of the patient at a target stimulation location.

4. The insertion kit of claim 1, wherein the fluid-insertion assembly comprises a mounting body configured and arranged for disposing over a portion of the jacket and forming a watertight seal between the fluid-insertion assembly and the lead body.

5. The insertion kit of claim 4, wherein the fluid-insertion assembly comprises at least one fluid-insertion port coupled to the mounting body.

6. The insertion kit of claim 4, wherein the fluid-insertion assembly comprises a fluid reservoir with an adjustable volume coupled to the mounting body, the fluid reservoir configured and arranged to empty its contents into the at least one first aperture via the mounting body.

7. The insertion kit of claim 1, wherein the fluid-insertion assembly comprises a syringe.

8. The insertion kit of claim 1, wherein the fluid-insertion assembly comprises at least one piston.

9. The insertion kit of claim 1, wherein the fluid input to the lead is a saline solution.

10. An electrical stimulating system comprising:
    the insertion kit of claim 1;
    a control module coupleable to the lead of the insertion kit, the control module comprising
        a housing, and
        an electronic subassembly disposed in the housing; and
    a connector for receiving the lead, the connector having a proximal end, a distal end, and a longitudinal length, the connector comprising
        a connector housing defining a port at the distal end of the connector, the port configured and arranged for receiving the proximal end portion of the lead body of the lead, and a plurality of connector contacts disposed in the connector housing, the plurality of connector contacts configured and arranged to couple to at least one of the plurality of terminals disposed on the proximal end portion of the lead body.

11. A method of implanting an electrical stimulation lead, the method comprising:
providing a lead that comprises a jacket that is disposed over at least a portion of a longitudinal length of a lead body of the lead and that forms at least a portion of an outer surface of the lead body, the lead defining a plurality of apertures disposed along the outer surface of the lead body with each of the plurality of apertures extending completely through the jacket, the plurality of apertures comprising at least one first aperture, the lead further comprising a plurality of electrodes disposed along a distal end portion of the lead body, a plurality of terminals disposed along a proximal end portion of the lead body, a plurality of conductors electrically coupling the plurality of electrodes to the plurality of terminals, and conductor insulation disposed over each of the plurality of conductors, wherein at least a portion of the conductor insulation is in fluid communication with the local environment external to the lead via the plurality of apertures;
inputting fluid into the at least one first aperture using a fluid-insertion assembly; and
advancing the lead with input fluid to a target stimulation location within a patient.

12. The method of claim 11, wherein inputting fluid into the at least one first aperture comprises inputting fluid into the at least one first aperture until an equilibrium is reached between the lead and interstitial fluid of the patient at the target stimulation location.

13. The method of claim 12, wherein inputting fluid into the at least one first aperture comprises inputting fluid into the at least one first aperture until open spaces in the lead are at least 30% filled, but less than completely filled.

14. The method of claim 12, wherein inputting fluid into the at least one first aperture comprises inputting fluid into the at least one first aperture until open spaces in the lead are at least 50% filled, but less than completely filled.

15. The method of claim 12, wherein inputting fluid into the at least one first aperture comprises inputting fluid into the at least one first aperture until open spaces in the lead are at least 70% filled, but less than completely filled.

16. The method of claim 12, wherein inputting fluid into the at least one first aperture comprises inputting fluid into the at least one first aperture until some of the input fluid flows out from the lead through at least one second aperture of the plurality of apertures, and wherein the at least one first aperture and the at least one second aperture are defined along opposing end portions of the lead body.

17. The method of claim 11, wherein inputting fluid into the at least one first aperture comprises inputting fluid directly into the at least one first aperture using a syringe.

18. The method of claim 11, wherein inputting fluid into the at least one first aperture comprises pushing fluid from a fluid reservoir into the at least one first aperture, the fluid reservoir coupled to a mounting body disposed over a portion of the lead body with the mounting body completely covering the at least one first aperture.

19. The method of claim 11, wherein inputting fluid into the at least one first aperture comprises inputting fluid into a fluid-input port coupled to a mounting body, the mounting body disposed over a portion of the lead body and completely covering the at least one first aperture.

* * * * *